United States Patent
Pedain et al.

(10) Patent No.: US 9,694,170 B2
(45) Date of Patent: Jul. 4, 2017

(54) METHOD AND DEVICE FOR PLANNING A DIRECT INFUSION INTO HEPATIC TISSUE

(71) Applicant: Brainlab AG, Feldkirchen (DE)

(72) Inventors: Christoph Pedain, Munich (DE); Andreas Hartlep, Naring (DE)

(73) Assignee: Brainlab AG, Munich (DE)

( * ) Notice: Subject to any disclaimer, the term of this patent is extended or adjusted under 35 U.S.C. 154(b) by 499 days.

(21) Appl. No.: 13/709,429

(22) Filed: Dec. 10, 2012

(65) Prior Publication Data

US 2014/0163514 A1  Jun. 12, 2014
US 2016/0015951 A9  Jan. 21, 2016

Related U.S. Application Data

(63) Continuation of application No. 11/533,116, filed on Sep. 19, 2006, now abandoned.
(Continued)

(30) Foreign Application Priority Data

Sep. 19, 2005  (EP) .................................... 05020406

(51) Int. Cl.
*A61M 5/14*  (2006.01)
*A61M 37/00*  (2006.01)
(Continued)

(52) U.S. Cl.
CPC ............ *A61M 37/00* (2013.01); *A61M 5/142* (2013.01); *A61B 2034/2055* (2016.02); *A61M 2005/14292* (2013.01); *A61M 2210/1071* (2013.01)

(58) Field of Classification Search
CPC ........ A61M 5/14; A61M 5/168; A61M 5/172; A61B 19/52443; A61B 19/5244
See application file for complete search history.

(56) References Cited

U.S. PATENT DOCUMENTS 5,010,473 A * 4/1991 Jacobs ........................... 700/30
5,865,744 A   2/1999 Lemelson
(Continued)

FOREIGN PATENT DOCUMENTS

EP  1 398 641  3/2004

OTHER PUBLICATIONS

Chandra et al., "The Complexities of Hepatic Drug Transport: Current Knowledge and Emerging Concepts", Pharmaceutical Research, vol. 21, No. 5, May 2004, pp. 719-735.
(Continued)

*Primary Examiner* — Tse Chen
*Assistant Examiner* — Jason Ip
(74) *Attorney, Agent, or Firm* — Tucker Ellis LLP

(57) ABSTRACT

A method for planning an infusion into hepatic tissue into a patient includes: obtaining anatomical and/or physiological patient data of the patient's liver or a region of the liver; determining at least one patient parameter from the patient data; planning the infusion using the anatomical patient data, physiological patient data, and/or at least one patient parameter, wherein planning includes determining how an administered substance is distributed in the tissue and/or how the administered substance influences physiological properties of the tissue; and determining a distribution and/or effectiveness of a therapeutic agent administered with the substance or after the substance.

19 Claims, 3 Drawing Sheets

Related U.S. Application Data

(60) Provisional application No. 60/724,038, filed on Oct. 6, 2005.

(51) Int. Cl.
*A61M 5/142* (2006.01)
*A61B 34/20* (2016.01)

(56) References Cited

U.S. PATENT DOCUMENTS

| | | | |
|---|---|---|---|
| 6,026,316 | A | 2/2000 | Kucharczyk et al. |
| 6,464,662 | B1 | 10/2002 | Raghavan et al. |
| 6,549,803 | B1 * | 4/2003 | Raghavan .............. A61M 5/14 382/128 |
| 6,722,370 | B1 | 4/2004 | Mann |
| 2002/0188275 | A1 | 12/2002 | McGuckin, Jr. |
| 2003/0114751 | A1 | 6/2003 | Pedain et al. |
| 2004/0009459 | A1 * | 1/2004 | Anderson ........... G06F 19/3406 434/262 |
| 2004/0010221 | A1 | 1/2004 | Pedain et al. |
| 2004/0057947 | A1 * | 3/2004 | Duettmann ............ A61K 33/06 424/94.64 |
| 2006/0093583 | A1 | 5/2006 | Hartlep et al. |

OTHER PUBLICATIONS

De Bruyn et al., "Sodium Fluorescein is a Probe Substrate for Hepatic Drug Transport Mediated by OATP1B1 and OATP1B3", Journal of Pharmaceutical Sciences, vol. 100, No. 11, Nov. 2011, pp. 5018-5030.

Fardel et al., "Regulation of human hepatic drug transporter expression by pro-inflammatory cytokines", http://informalhealthcare.com, vol. 5, No. 12, Dec. 2009, pp. 1469-1481.

Feely, M.D. et al., "Reduction of Liver Blood Flow and Propranolol Metabolism by Cimetidine", The New England Journal of Medicine, vol. 304, No. 12, Mar. 1981, pp. 692-695.

Nakamoto et al., "A New Method of Antitumor Therapy with a High Dose of TNF Perfusion for Unresectable Liver Tumors", Anticancer Research, vol. 20, 2000, pp. 4087-4096.

Oldhafer, M.D. et al., "First experience and technical aspects of isolated liver perfusion for extensive liver metastasis", Departments of Abdominal and Transplantation Surgery, Radiology, and Hematology and Oncology, and the Institute of Pathology, Hannover Medical School, vol. 123, No. 6, Nov. 1997, pp. 622-631.

Rothbarth et al., "Isolated hepatic perfusion with high-dose melphalan for the treatment of colorectal metastasis confined to the liver", British Journal of Surgery 2003, pp. 1391-1397.

Verzaro, M.D. et al., "A Safe and Fast Technique for Isolated Hepatic Perfusion", Journal of Surgical Oncology, vol. 98, 2008, pp. 393-396.

Keat, "Real-time CT and CT fluoroscopy", Brit J Radio, 2001, pp. 1088-1090.

Maeda, "The Enhanced Permeability and Retention (EPR) Effect in Tumor Vasculature: The Key Role of Tumor-selective Macromolecular Drug Targeting", Advanced Enzyme Regulation, vol. 41, 2001, pp. 189-207.

* cited by examiner

METHOD AND DEVICE FOR PLANNING A DIRECT INFUSION INTO HEPATIC TISSUE

RELATED APPLICATION DATA

This application is a continuation of U.S. application Ser. No. 11/533,116, filed on Sep. 19, 2006, which claims priority of U.S. Provisional Application No. 60/724,038 filed on Oct. 6, 2005, both of which are incorporated herein by reference in their entirety.

FIELD OF THE INVENTION

The present invention relates to a method and device for planning an infusion, in particular a direct infusion, into hepatic tissue.

BACKGROUND OF THE INVENTION

In order to treat a diseased liver, such as a cancerous liver, drugs can be directly dispensed into the target tissue. Since vascularisation in the liver is high, many vessels (e.g., blood vessels) pass through the liver. As a result, substances fed to the liver often outflow from the liver to other parts of the body.

Techniques exist for influencing the perfusion of hepatic tissue. If perfusion in the tissue can be reduced, the retention period of the administered substance within the liver can be extended, and the therapeutic effect can be correspondingly improved, while simultaneously diminishing side-effects.

For treating liver cancer, a technique called transarterial chemoembolisation (TACE) is known, wherein the blood supply to a tumor is interrupted and chemotherapy is administered directly on the tumor. The chemotherapeutic agents, for example, can be injected into the hepatic artery leading to the hepatoma. In chemoembolisation, additional material may be injected to block small branches of the hepatic artery. It is very likely, however, that a considerable portion of the chemotherapeutic agents will enter other parts of the body. Selective intra-arterial chemotherapy can therefore cause the usual systematic side-effects that affect the entire body. This treatment also can lead to a number of side-effects that regionally affect particular parts of the body, such as, for example, inflammation of the gallbladder (cholecystitis), intestinal or stomach ulcers and inflammation of the pancreas (pancreatitis). Liver failure also can occur after such treatment in patients with hepatocellular carcinoma (HCC) and advanced cirrhosis.

Other methods for treating the liver include attaching radioactive material to antibodies that are directed at particular target areas in liver cancer cells (immunotherapy). A method and device for administering a substance is known from EP 1 316 324 A1 belonging to the Applicant.

SUMMARY OF THE INVENTION

In a non-surgical and non-therapeutic method for planning an infusion, in particular a direct infusion, into the liver or into hepatic tissue, anatomical and/or physiological patient data can be individually captured for a patient to be treated. Patient data or patient parameters obtained from patient data, for example, can be obtained using known nuclear spin resonance (MRI) methods, computer tomography (CT) methods, angiography, perfusion imaging, PET, SPECT, biopsy, x-ray methods, and/or ultrasound methods. Other suitable methods that enable the spatial structure of a body, in particular the tissue structure of a body such as, for example, the liver and the surrounding tissue, to be detected and displayed, and/or functional data such as patient-specific diffusion and perfusion properties or data regarding blood pressure also may be used. In addition, data stored beforehand in a database also can be used to evaluate obtained data, for example, by means of an imaging method and to assign the data to particular types of tissue, structures or properties such as the degree of blood flow, for example.

The execution of liver infusion can be planned using the ascertained patient data, e.g., by taking into account different selectable presets. These presets can include, for example, the patient data or also parameters of available substances to be administered, such as, for example, chemotherapeutic agents (e.g., drug, medicine, toxin, microspheres such as capsules made of proteins and that can contain an active agent and can have a size in the sub-millimeter to nanometer range, liposomes, radioactive substances, gases, hormones, . . . ), parameters of catheters and/or pumps that may be used. A suitable selection can be made, for example, for a physiologically active substance administered before the infusion agent and/or for the infusion agent and/or catheter to be used, the positioning of the catheter can be simulated, planned or performed with regard to its attachment location and depth of penetration, the substance and/or infusion agent can be modified if necessary, for example changed in its concentration (e.g., diluted), and the time course of the pressure with which the substance and/or infusion agent is to be fed through one or more catheters may be pre-set, for example. The aim of such selecting and setting is to introduce into a target tissue volume of the liver a defined amount of the substance to be administered with the infusion agent, to obtain a particular concentration within said target tissue volume, wherein as little as possible of the substance to be administered is to be introduced into non-targeted tissues.

The time course of the distribution of the substance and/or the infusion agent, for example in the liver, and/or the uptake of the infusion agent by or in the tissue and/or the interaction with other administered substances, for example, can be calculated and displayed at different time points.

By using two or more substances or infusion agents administered together or separately, for example, it is possible to influence physiological properties such as, for example, the blood flow in a region of tissue, in order to extend the retention period in the tissue to be treated of a subsequently administered therapeutic agent.

It is possible to calculate the distribution of an infusion agent and/or substance that influences transport processes in the target region or target tissue, such as, for example, blood flow and/or perfusion in the liver, or the impact on this distribution of a substance, for example, administered before the infusion agent, wherein the infused substance influences physiological properties. It is possible to calculate the effects of the treatment, e.g., the possible effectiveness of an infusion agent or of a physiologically active substance administered before, after, together with or as the infusion agent, and the region or regions influenced by these effects at different time points after the substance has been administered. Such effects can include, for example, a diminishing of the blood flow in a particular region of the liver by the infused substance, in order to increase the time of effectiveness and/or concentration of the infusion agent in a particular region. Based on the calculation of the distribution of an infusion agent, such as, for example, a therapeutic agent, and of the distribution or impact of an effect of the therapeutic agent, it is possible to simulate the effectiveness of the agent on a tissue and to optionally change the infusion plan.

It is thus possible to calculate and simulate the distribution of substances which are directly administered into hepatic tissue or the impact of such a distribution of the substance, and therefore to calculate and simulate a successful treatment by administering such substances. This enables a physician to determine the outcome of a treatment based on directly administering substances, such as, for example, drugs and/or energy (e.g., heat) and/or based on simulating the distribution of the substance, in order to produce an optimized treatment plan for a patient based on the patient's individual anatomy and physiological properties. This can lead to an optimization of the treatment effects and thus to a more successful treatment, while simultaneously diminishing side-effects. Consequently, it is no longer necessary, as in the prior art, to estimate the uptake of the substance by tissues based on the individual experience of a physician, but rather a treatment can be optimized individually for a patient, using known effective mechanisms.

The captured patient data can be used to position the infusion device(s), for example one or more catheters, wherein the patient data can be used to ascertain where in the patient's body a tissue volume to be treated, such as a hepatoma, for example, is situated. Using this information, a suitable catheter, for example, can be manually selected (e.g., by a user) or automatically selected from an available database, and modified as applicable by post-processing (e.g., cutting the catheter to length application-specifically or patient-specifically with respect to the desired depth of penetration into the tissue). It also is possible to ascertain a suitable point for attaching the catheter, in order for the infusion to burden healthy tissue as little as possible.

Known methods for positioning, such as, for example, using reflective markers attached to the catheter and detected by infrared cameras or by magnetic coils which detect a defined external magnetic field, can advantageously be used to attach the catheter at a desired position on the patient. Markers also can be attached to the patient him/herself, which serve as a reference and can be used to define a patient coordinate system within which the catheter is positioned at a particular ascertained point.

Using the ascertained patient data for planning the infusion, patient-specific parameters preferably are ascertained, such as for example the tissue structure or body structure in the region of the tissue to be treated by infusion. It is particularly advantageous to ascertain the tissue density, distribution of particular tissue structures, or the blood flow in a particular region of tissue as patient parameters. Patient parameters can be obtained both directly from the captured patient data and from databases, or from a combination of values stored in databases together with the captured patient data. Values relating to the usual blood flow, in particular regions of tissue, the diffusion and perfusion behavior of selected substances in the relevant tissue, and values relating to the behavior of the tissue after a known substance has been supplied (e.g., swelling of the tissue or metabolic reactions) can thus be stored in databases and can be used as patient parameters for planning an infusion.

It is also advantageous to ascertain infusion agent parameters that are characteristic of the substance to be administered or of an active agent and which, for example, define the physical, chemical and/or biological properties. Information relating to the molecular or particle size of the substance to be administered, the rate of diffusion of said substance in a particular type of tissue, the metabolism and/or interaction of the substance with tissue due to metabolic processes, a diffusion coefficient known for the substance and type of tissue to be treated or an advantageous injection pressure or pressure gradient, an advantageous concentration, amount or supply rate, the order of magnitude of which usually lies in the ml/h range, can be obtained from a database, for example. The infusion agent parameters listed by way of example can be used individually or in combination, together with other parameters for planning the infusion.

Catheter parameters, e.g., variables specific to a catheter, can be advantageously used for planning the infusion, wherein different types of catheters can be provided for selection in a database. Catheter parameters relevant to the infusion, for example, can be the inner diameter of the catheter, the surface characteristics, the material, in particular the rigidity of the catheter, the number and arrangement of the exit openings on the catheter, or a known suitability of a particular type of catheter for a particular substance to be administered or a particular type of tissue or tissue disease to be treated. In general, multiple catheters also can be used.

A drug, toxin, microspheres, liposomes, radioactive substances, gases, hormones, a solution containing cells, viruses, genes, enzymes, proteins, hormones, antibodies or a combination of these, for example, can be used as the infusion agent.

By using the patient parameters, infusion agent parameters and/or catheter parameters cited above by way of example, individually or in combination, together with the captured patient data, it is possible to plan an infusion, such that as large a proportion of a substance as possible is introduced by infusion into a target region of tissue of the liver, wherein as little as possible of the substance is dispensed into non-targeted tissues. Thus, a substance to be introduced into tissues by infusion can be introduced into a patient's region of tissue to be treated using a particularly suitable and correctly positioned type of catheter and the correct injection pressure, in a desired concentration at a desired rate, and taking into account metabolic and diffusion processes, in order to obtain a desired concentration of the substance to be introduced in said region of tissue, wherein surrounding tissue is burdened as little as possible.

For forward planning of the infusion, the infusion to be performed can be simulated, for example by calculating the distribution of the infusion agent in tissue, using the captured patient data and the different aforesaid parameters. Using such a simulation, it is possible to ascertain the distribution of the infusion agent both statically and dynamically as a function of time and graphically display the distribution. It is thus possible, even before performing an infusion, to determine whether a desired concentration distribution of the substance to be introduced can be obtained in the target tissue, or whether infusion agent parameters, catheter parameters or patient parameters have to be changed as applicable in order to ensure a more successful infusion.

Reverse or inverse planning also can be performed, wherein, for example, an operator pre-sets particular treatment data such as the target volume to be treated, advantageously together with risk structures such as nerve tracts which should not be impaired by the infusion, and details of the type of tissue to be treated, wherein the sequence of the infusion can be defined either automatically or in interaction with the user, for example by displaying a selection menu, e.g, one or more types of catheter can be selected together with suitable infusion agents, the catheter arrangement(s) can be defined with regard to position and/or depth of penetration, and the infusion agent parameters can be set, in order to enable as optimum an infusion treatment as possible for the pre-set target volume.

The planning methods described above, in particular selecting the individual parameters, can be performed automatically, for example using values stored in one or more databases, semi-automatically, for example by selections made by a user from a displayed menu, or manually, for example by parameter values to be input by a user. Suitable computers, together with input and output elements (e.g., display elements) can be used with the automatic, semi-automatic and manual implementations. The display elements can provide visual representations of elements to be selected, tissue structures, calculated concentration distributions of the infusion agent in the tissue, and other information.

In accordance with another aspect of the invention, there is provided a computer program which, when it is loaded onto a computer or is running on a computer, performs the method described above or parts of it. Further, a storage medium for such a program or to a computer program product comprising the aforementioned program also is provided.

A device for planning a liver infusion comprises a planning system including a computer system, preferably with input and output devices and corresponding software, wherein a monitor is advantageously provided for displaying elements pre-set by the computer from databases or values and/or spatial distributions ascertained from calculations.

A navigation system is also advantageously provided which, for example, can include reflective markers, LEDs or coils attached to elements to be positioned, and infrared cameras or magnetic field generators. Using the navigation system, a catheter, for example, can be precisely positioned on a body using a suitable known software and/or hardware.

In general, the device can include elements, devices and systems that can be used to perform the method steps described above.

In accordance with another aspect of the invention, there is provided a liver infusion method, wherein the infusion is preferably prepared as described above and the infusion agent is subsequently introduced into the body or hepatic tissue.

Advantageously, a verification or check can be continuously performed during the infusion or at particular time intervals, wherein the distribution of the infusion agent in the tissue during or after the infusion procedure is ascertained using a suitable data capture or imaging system. Nuclear spin resonance or ultrasound methods, for example, can be used as the data capture or imaging system, wherein it can be advantageous to add a contrast medium to the infusion agent to clearly determine or measure the distribution of the infusion agent in the body tissue.

Preferably, deviations between the actual distribution of the infusion agent in the tissue as ascertained in the verification procedure and the planning data as ascertained before or during the infusion are determined and preferably displayed. The infusion parameters can be corrected, e.g., the chemical and/or physical composition or properties of the infusion agent can be changed and/or the supply changed, for example the injection pressure or the amount dispensed can be changed, to be able to correct the deviation from the planned distribution, as ascertained during verification. If necessary, a catheter can also be repositioned or exchanged.

Verification, ascertaining the deviation and correcting are advantageously performed in real time, such that the infusion can be performed in a regulated way via a feedback, in order to obtain the desired successful infusion, e.g., in order to supply the infusion agent to the pre-set target region as desired.

In accordance with another aspect of the invention, there is provided a computer program which, when it is loaded onto a computer or is running on a computer, performs the method described above. Further, a storage medium for such a program or to a computer program product comprising the aforementioned program can be provided.

In accordance with another aspect of the invention, there is provided a device for performing an infusion method as described above, comprising a verification device for ascertaining the spatial distribution of an infusion agent in a body, in particular in a region of tissue. The verification device, for example, can be a nuclear spin resonance system, an x-ray system or an ultrasound system, using which the infusion agent or its distribution or concentration in the tissue can be detected.

Advantageously, a computer system can be provided with a display device for evaluating the ascertained spatial distribution of the infusion agent in the tissue, determining a deviation from an infusion plan defined beforehand, and automatically changing infusion parameters as applicable, or suggesting such a change to an operator, in order to modify the infusion such that it can be performed as planned. To this end, systems, for example, can be provided that can change the concentration of the infusion agent and/or the injection pressure or injected amount, for example by means of a pump, to obtain a distribution of the infusion agent in the tissue as planned beforehand. Advantageously, the type and size of the change in the infusion parameters, when a deviation from a pre-set infusion plan is determined during verification, is ascertained using known effective and functional mechanisms. The supply rate or injection pressure can be diminished, for example, if it is determined that the infusion agent is dispersing faster than predetermined or is not being degraded by metabolic processes as fast as expected.

BRIEF DESCRIPTION OF THE DRAWINGS

The forgoing and other embodiments of the invention are hereinafter discussed with reference to the drawings.

DETAILED DESCRIPTION

Figure 1:
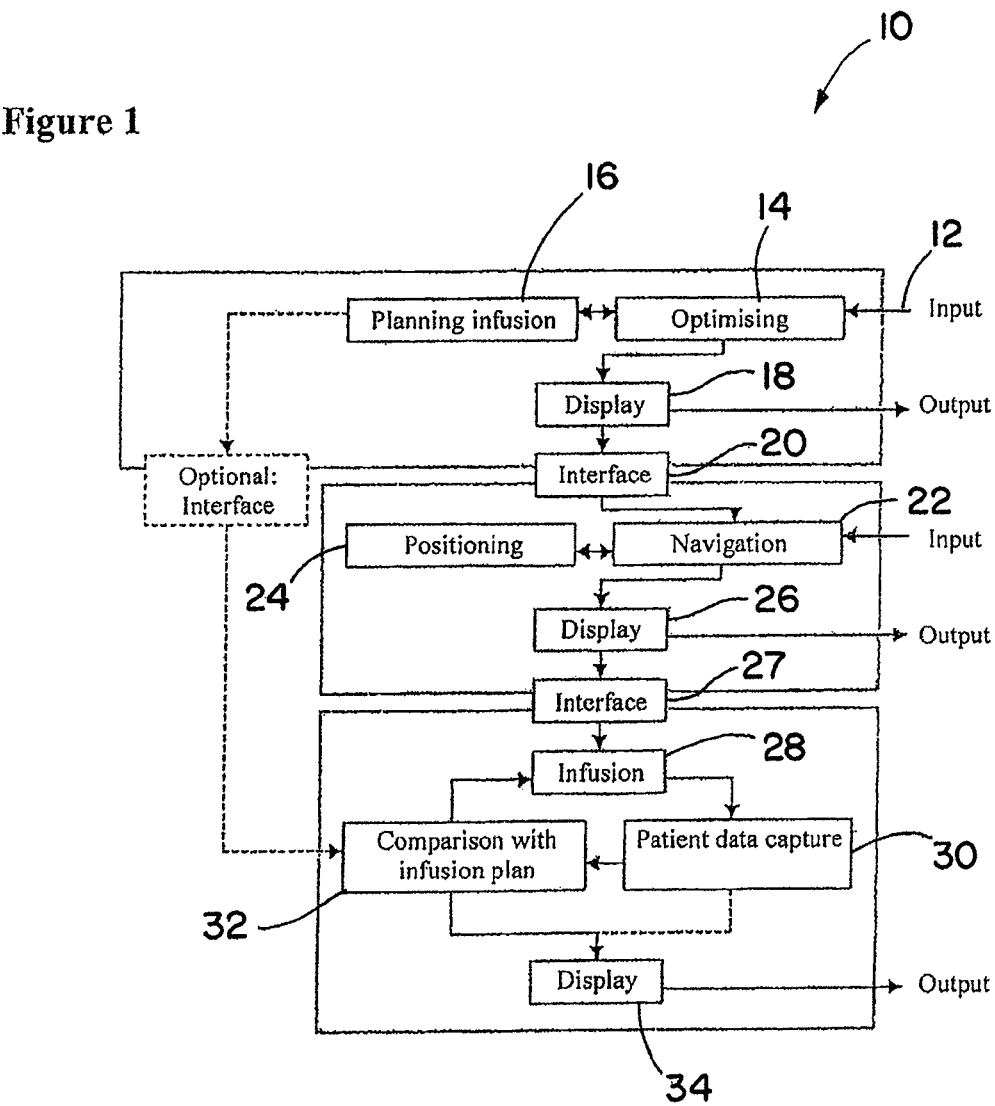
FIG. 1 is a schematic diagram of an exemplary method for planning and performing a liver infusion in accordance with the invention.

FIG. 1 schematically shows a flow diagram 10 for preparing and performing an exemplary liver infusion. As shown in FIG. 1, at block 12 patient data, for example, are input from a nuclear spin tomograph and used to ascertain a particular target region of tissue in the liver (e.g., in or in the vicinity of a hepatoma) for the infusion and to plan the infusion dosage to be supplied. These data can be obtained by the nuclear spin resonance system 60, for example, as shown schematically in FIG. 3, once a patient to be treated has been examined. Using parameters for the properties of the tissue structures, infusion agents and different types of catheters, one or more infusion agents and/or catheters which are suitable for the infusion can be selected once the exact position of the tissue volume to be treated has been ascertained. The parameters, for example, can be stored in one or more databases. At blocks 14 and 16, the patient parameters obtained, for example, by the nuclear spin resonance method, together with the catheter parameters and the infusion agent parameters (also stored in databases, for example), can be used to plan the infusion, wherein the corresponding parameters can be optimized subject to the ancillary condition that as large a proportion of the infusion agent as possible is introduced into the hepatic tissue at a desired concentration, wherein as little infusion agent as possible is to enter tissue outside the hepatic tissue. In general, as few catheters or needles as possible should be positioned, and supplied by as few feeds as possible. This optimized plan for the infusion dosage can be output via a display, as indicated at block 18. For example, a two-dimensional or three-dimensional representation can be output by imaging different incision planes, in order to display the outcome of the infusion plan.

Figure 3:
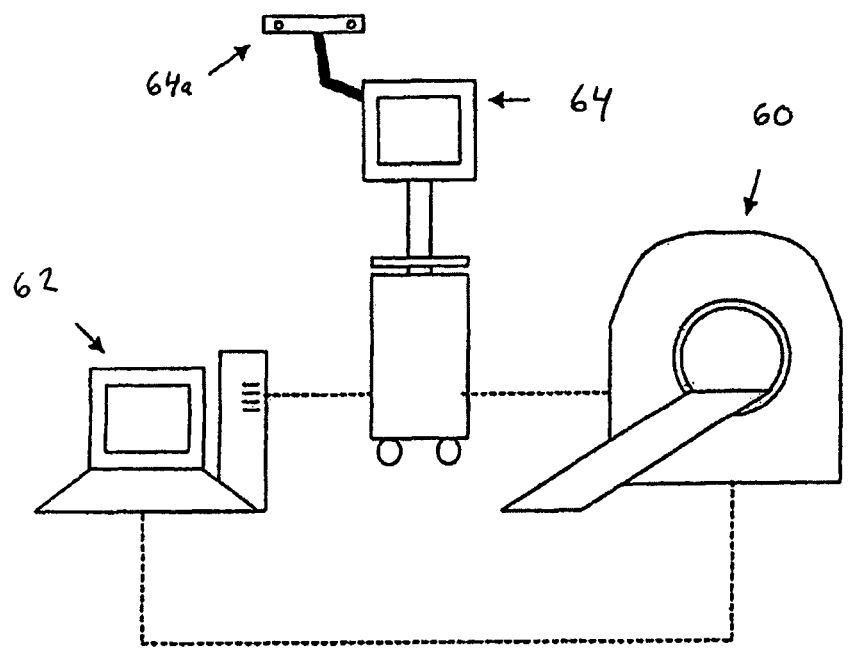
FIG. 3 is an exemplary device which can be used in planning and performing an infusion in accordance with the invention.

The infusion plan thus produced can be transmitted at blocks 20 and 22 via an interface to a navigation system, such as for example the VectorVision™ system shown schematically in FIG. 3, in order to position the selected catheter or catheters on the pre-set points on the body based on the planning data. The catheter or catheters can be positioned automatically, for example using a robot, or manually positioned with guidance from the navigation system, wherein it is possible to display on a display device whether a catheter is correctly positioned or still has to be moved in a particular direction, as indicated at blocks 24 and 26.

Once the catheter or catheters have been successfully positioned, the infusion is performed at block 28 using the infusion agent parameters pre-set by the plan, wherein patient data can be again captured at block 30 in order to ascertain the actual distribution of the infusion agent in the hepatic tissue. Using the parameters pre-set by the plan and the simulation results for the infusion based on parameters, at block 32 a comparison can be made between the actual distribution of the infusion agent and the predetermined, desired distribution of the infusion agent. Based on the comparison, the parameters, such as for example the concentration of the infusion agent, the amount dispensed or the injection pressure for performing the infusion, can be altered as applicable, taking into account known effective mechanisms, in order to obtain the desired, planned outcome of the infusion. The actual measured distribution of the concentration of the infusion agent, preferably together with any deviations and correction procedures, can again be output via a display at block 34, in order to enable an operator to manually intervene in the injection method, for example.

Figure 2:
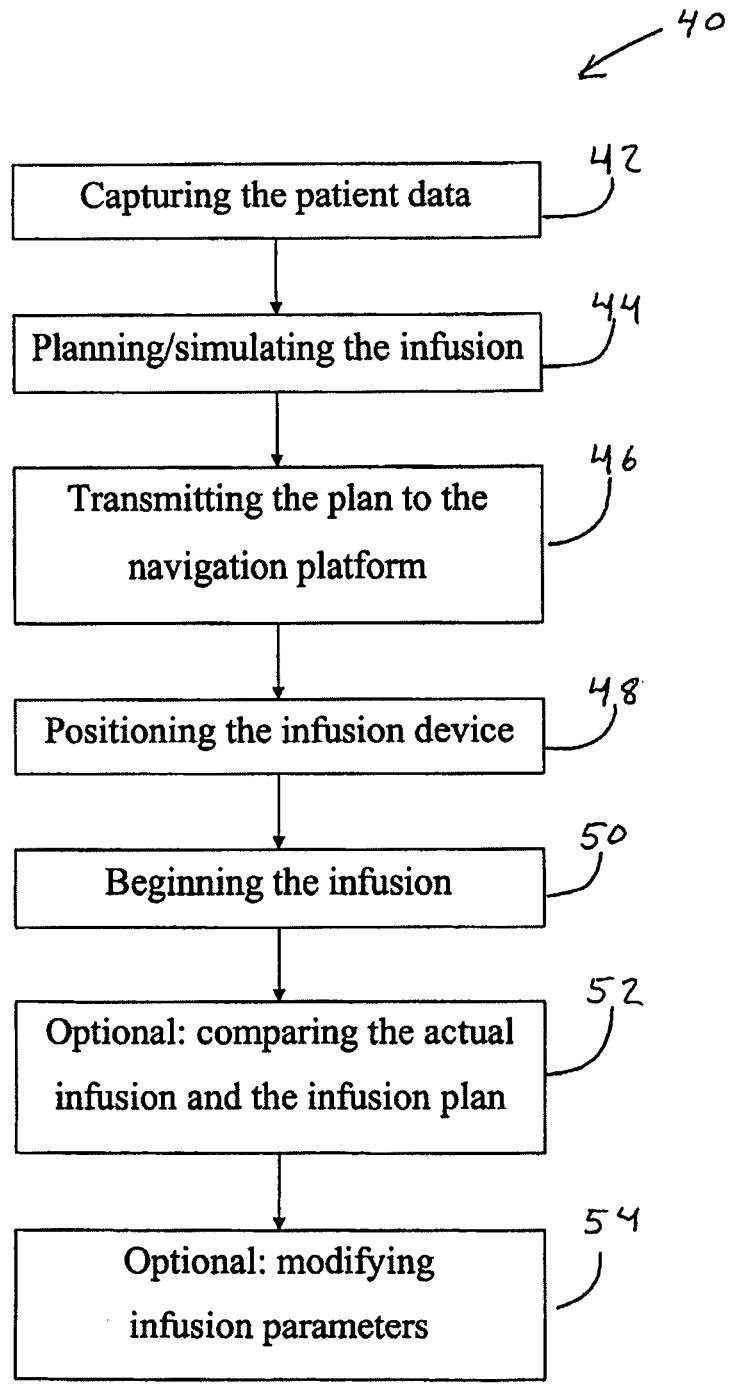
FIG. 2 is a simplified flow diagram of an exemplary infusion performed in accordance with the invention.

FIG. 2 schematically shows a simplified sequence 40 of planning and performing an exemplary liver injection. Firstly, at block 42 patient data can be captured by an imaging diagnostic method such as, for example, a nuclear spin resonance method, in order to obtain the current patient parameters such as, for example, tissue density, blood flow and the position of hepatic tissue to be treated. At block 44, the infusion can be planned and/or simulated using the patient parameters thus ascertained, together with catheter and infusion agent parameters obtained from a database and/or pre-set for a particular infusion. Based on the parameter data thus ascertained, the infusion plan can be relayed to a navigation platform at block 46. At block 48, the navigation platform can be used to position the catheter or catheters on the patient, as provided for in the infusion plan. At block 50, the infusion begins once the infusion device has been positioned and is performed using the planned and as applicable simulated parameters, wherein at block 52, a comparison can be made between the infusion actually performed and the infusion plan at block 52, and if there are deviations, a modification can be made to the corresponding parameters, preferably utilizing known effective mechanisms at block 54.

FIG. 3 schematically shows a device which can be used for planning and performing an infusion. Patient data can be obtained in a nuclear spin tomograph 60 and relayed to a planning system 62 and a navigation system 64. Using known reflectors or markers attached to one or more catheters, the catheter or catheters are positioned on a desired point on a body using the navigation system 64, wherein positional data of the markers are detected by infrared cameras 64a. Using the patient parameters ascertained by the nuclear spin resonance system 60, the planning system 62 ascertains, for a pre-set infusion to be performed, the suitable catheter parameters and infusion agent parameters for performing the infusion.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for planning an infusion into hepatic tissue of an associated patient, the method comprising:
   a. presetting a treatment result distribution and concentration of a therapeutic infusion agent in the hepatic tissue of the associated patient;
   b. obtaining anatomical patient data of the hepatic tissue;
   c. obtaining physiological patient data of the hepatic tissue;
   d. ascertaining an initial infusion parameter for infusing the therapeutic infusion agent into the hepatic tissue, the ascertaining being based on the preset treatment result distribution and concentration, the anatomical patient data of the hepatic tissue, and the physiological patient data of the hepatic tissue;
   e. simulating, using a processor, a distribution of the therapeutic infusion agent in the hepatic tissue, the simulating being based on the initial infusion parameter, wherein the simulating comprises:
      calculating, as a first simulation result, a simulated distribution in the hepatic tissue of a physiologically active substance administered to the hepatic tissue and a simulated influence on the hepatic tissue of the physiologically active substance administered to the hepatic tissue, the physiologically active substance influencing one or more transport processes to reduce blood flow in the hepatic tissue, and the physiologically active substance being different than the therapeutic infusion agent and being administered to the hepatic tissue separately from and before an administration of the therapeutic infusion agent to the hepatic tissue thereby increasing a time effectiveness and/or concentration of the therapeutic infusion agent by the reduced blood flow in the hepatic tissue; and calculating, based on the first simulation result, the simulated distribution of the therapeutic infusion agent administered in the hepatic tissue after the physiologically active substance is administered to the hepatic tissue;

f. comparing a result of the simulating with the preset treatment result distribution and concentration of the therapeutic infusion agent in the hepatic tissue;

g. revising the initial infusion parameter based on the comparing to optimize the treatment result distribution and concentration of the therapeutic infusion agent in the hepatic tissue; and h. iteratively performing steps a-g to obtain an infusion plan having a greater concentration of the therapeutic infusion agent in a target tissue relative to a non-target tissue or a smaller concentration of the therapeutic infusion agent in the non-target tissue relative to the target tissue, wherein at least one parameter of the therapeutic infusion agent, at least one parameter of the infusion, or at least one parameter of an associated catheter is changed for subsequent one or more iterations.

2. The method according to claim 1, wherein the presetting the treatment result comprises presetting a distribution of the therapeutic infusion agent in a target volume.

3. The method according to claim 1, wherein the ascertaining the initial infusion parameter comprises ascertaining at least one of a position of the associated catheter, a depth of penetration of the associated catheter, or a parameter of the therapeutic infusion agent.

4. The method according to claim 1, wherein the obtaining the anatomical and the physiological patient data of the hepatic tissue comprises using at least one of a nuclear spin resonance method, an x-ray method, angiography, perfusion imaging, PET, SPECT, biopsy, or an ultrasound method to obtain the at least one of the anatomical or the physiological patient data of the hepatic tissue.

5. The method according to claim 1, wherein the simulating the distribution of the therapeutic infusion agent in the hepatic tissue further comprises using a mathematical model to simulate the distribution based on at least one of a parameter of the associated catheter, a parameter of the therapeutic infusion agent, or a parameter of the associated patient.

6. The method according to claim 5, wherein using the mathematical model to simulate the distribution of the therapeutic infusion agent in the hepatic tissue comprises using at least one of properties or parameters of the physiologically active substance or a therapeutic agent to be injected, patient-related data, data from a treatment report or data from a database, in order to calculate the distribution of the therapeutic infusion agent in the hepatic tissue.

7. The method according to claim 5, further comprising calculating from the mathematical model an anatomical or patient-related image for selective display of the distribution of the therapeutic infusion agent on an associated human readable display device.

8. The method according to claim 1, further comprising executing the infusion plan.

9. The method according to claim 8, further comprising comparing actual infusion data with planned infusion data.

10. The method according to claim 9, wherein the comparing the actual infusion data with the planned infusion data comprises ascertaining one or more deviations between the planned infusion data and the actual infusion data.

11. The method according to claim 10, further comprising correcting the infusion plan based on the ascertained one or more deviations.

12. A non-transitory computer readable medium storing a program which, when running on a computer or loaded onto the computer, performs a method for planning an infusion into hepatic tissue of an associated patient, the method comprising:

a. receiving as a user input a preset treatment result distribution and concentration of a therapeutic infusion agent in the hepatic tissue of the associated patient;

b. obtaining anatomical patient data of the hepatic tissue;

c. obtaining physiological patient data of the hepatic tissue;

d. ascertaining an initial infusion parameter for infusing the therapeutic infusion agent into the hepatic tissue, the ascertaining being based on the preset treatment result distribution and concentration, the anatomical patient data of the hepatic tissue, and the physiological patient data of the hepatic tissue;

e. simulating a distribution of the therapeutic infusion agent in the hepatic tissue based on the initial infusion parameter, wherein the simulating comprises:

calculating, as a first simulation result, a simulated distribution in the hepatic tissue of a physiologically active substance administered to the hepatic tissue and a simulated influence on the hepatic tissue of the physiologically active substance administered to the hepatic tissue, the physiologically active substance influencing one or more transport processes to reduce blood flow in the hepatic tissue, and the physiologically active substance being different than the therapeutic infusion agent and being administered to the hepatic tissue separately from and before an administration of the therapeutic infusion agent to the hepatic tissue thereby increasing a time effectiveness and/or concentration of the therapeutic infusion agent by the reduced blood flow in the hepatic tissue; and calculating, based on the first simulation result, the distribution of the therapeutic infusion agent administered in the hepatic tissue after the physiologically active substance is administered to the hepatic tissue;

f. comparing a result of the simulating with the preset treatment result distribution and concentration of the therapeutic infusion agent in the hepatic tissue;

g. revising the initial infusion parameter based on the comparing to optimize the treatment result distribution and concentration of the therapeutic infusion agent in the hepatic tissue; and h. iteratively performing steps a-g to obtain an infusion plan having a greater concentration of the therapeutic infusion agent in a target tissue relative to a non-target tissue or a smaller concentration of the therapeutic infusion agent in the non-target tissue relative to the target tissue, wherein at least one parameter of the therapeutic infusion agent, at least one parameter of the infusion, or at least one parameter of an associated catheter is changed for subsequent one or more iterations.

13. A system for planning an infusion into hepatic tissue of an associated patient, the system comprising:

a patient data capture system for capturing patient data;

a planning system configured to plan the infusion based on the captured patient data, said planning system operatively coupled with the patient data capture system and operative to plan the infusion using patient data captured by the patient data capture system, wherein the planning system is configured to perform a method comprising:
a. receiving, as a user input, a preset treatment result distribution and concentration of a therapeutic infusion agent in the hepatic tissue of the associated patient;
b. obtaining anatomical patient data of the hepatic tissue;
c. obtaining physiological patient data of the hepatic tissue;
d. ascertaining an initial infusion parameter for infusing the therapeutic infusion agent into the hepatic tissue, the ascertaining being based on the preset treatment result distribution and concentration and the at least one of the anatomical or the physiological patient data of the hepatic tissue;
e. simulating a distribution of the therapeutic infusion agent in the hepatic tissue based on the initial infusion parameter, wherein the simulating comprises:
calculating, as a first simulation result, a simulated distribution in the hepatic tissue of a physiologically active substance administered to the hepatic tissue and a simulated influence on the hepatic tissue of the physiologically active substance administered to the hepatic tissue, the physiologically active substance influencing one or more transport processes to reduce blood flow in the hepatic tissue, the and physiologically active substance being different than the therapeutic infusion agent and being administered to the hepatic tissue separately from and prior to an administration of the infusion agent to the hepatic tissue thereby increasing a time effectiveness and/or concentration of the therapeutic infusion agent by the reduced blood flow in the hepatic tissue; and
calculating, based on the first simulation result, the simulated distribution of the infusion agent administered in the hepatic tissue after the physiologically active substance is administered to the hepatic tissue;
f. comparing a result of the simulating with the preset treatment result distribution and concentration of the therapeutic infusion agent in the hepatic tissue;
g. revising the initial infusion parameter based on the comparing to optimize the treatment result distribution and concentration of the therapeutic infusion agent in the hepatic tissue; and
h. iteratively performing steps a-g to obtain an infusion plan having a greater concentration of the therapeutic infusion agent in a target tissue relative to a non-target tissue or a smaller concentration of the therapeutic infusion agent in the non-target tissue relative to the target tissue, wherein at least one parameter of the therapeutic infusion agent, at least one parameter of the infusion, or at least one parameter of an associated catheter is changed for subsequent one or more iterations.

14. The system according to claim 13, further comprising a navigation system for positioning at least one catheter for administering the therapeutic infusion agent based on the infusion plan.

15. The system according to claim 13, wherein the system is further operative to compare planned hepatic tissue infusion data with actual hepatic tissue infusion data.

16. The system according to claim 15, wherein the system is further operative to correct one or more deviations between the actual hepatic tissue infusion data and the planned hepatic tissue infusion data.

17. The method according to claim 1, wherein:
the calculating as the first simulation result the simulated distribution in the hepatic tissue of the physiologically active substance administered to the hepatic tissue and the simulated influence on the hepatic tissue of the physiologically active substance administered to the hepatic tissue comprises:
calculating, as the first simulation result, the simulated distribution in the hepatic tissue and the simulated influence on the hepatic tissue of two or more physiologically active substances administered to the hepatic tissue; and
the calculating, based on the first simulation result, the simulated distribution of the therapeutic infusion agent administered in the hepatic tissue comprises:
calculating the simulated distribution of the therapeutic infusion agent administered in the hepatic tissue during or after the two or more physiologically active substances are administered to the hepatic tissue.

18. The non-transitory computer readable medium according to claim 12, wherein:
the calculating as the first simulation result the simulated distribution in the hepatic tissue of the physiologically active substance administered to the hepatic tissue and the simulated influence on the hepatic tissue of the physiologically active substance administered to the hepatic tissue comprises:
calculating, as the first simulation result, the simulated distribution in the hepatic tissue and the simulated influence on the hepatic tissue of two or more physiologically active substances administered to the hepatic tissue; and
the calculating, based on the first simulation result, the simulated distribution of the therapeutic infusion agent administered in the hepatic tissue comprises:
calculating the simulated distribution of the therapeutic infusion agent administered in the hepatic tissue during or after the two or more physiologically active substances are administered to the hepatic tissue.

19. The system according to claim 13, wherein:
the calculating as the first simulation result the simulated distribution in the hepatic tissue of the physiologically active substance administered to the hepatic tissue and the simulated influence on the hepatic tissue of the physiologically active substance administered to the hepatic tissue comprises:
calculating, as the first simulation result, the simulated distribution in the hepatic tissue and the simulated influence on the hepatic tissue of two or more physiologically active substances administered to the hepatic tissue; and
the calculating, based on the first simulation result, the simulated distribution of the therapeutic infusion agent administered in the hepatic tissue comprises:
calculating the simulated distribution of the therapeutic infusion agent administered in the hepatic tissue during or after the two or more physiologically active substances are administered to the hepatic tissue.

* * * * *